United States Patent [19]

Powers

[11] 4,206,630
[45] Jun. 10, 1980

[54] SAMPLE CHAMBER FOR GAS ANALYZER

[75] Inventor: Howard A. Powers, Sunnyvale, Calif.

[73] Assignee: Econics Corporation, Cupertino, Calif.

[21] Appl. No.: 19,640

[22] Filed: Mar. 12, 1979

[51] Int. Cl.² .......................................... G01N 21/26
[52] U.S. Cl. .............................. 73/1 G; 73/421.5 A; 356/438
[58] Field of Search ........................ 73/1 G, 421.5 R; 356/437, 438, 439, 440; 250/576; 350/63

[56] References Cited

U.S. PATENT DOCUMENTS 1,969,626  8/1934  Simon .................................. 356/438
3,847,487  11/1974  Boll ..................................... 356/438

FOREIGN PATENT DOCUMENTS 1039955  8/1966  United Kingdom ...................... 350/63

OTHER PUBLICATIONS

Webb, True On-Line and Span Determination for Continuous Emission Monitoring System.

Primary Examiner—S. Clement Swisher
Attorney, Agent, or Firm—Limbach, Limbach & Sutton

[57] ABSTRACT

A sample chamber for a gas analyzer for use in a duct containing gases to be analyzed is disclosed and includes a flow directing apparatus formed by a pair of spaced members which form a passage therebetween in the form of a converging diverging throat and an outer housing at least partially surrounding the flow directing apparatus. This outer housing has at least a pair of apertures and is movable by a suitable apparatus between one position in which the outer housing apertures are generally aligned with the flow directing passage and another position in which the outer housing apertures are spaced from the passage with non-apertured portions of the outer housing positioned across the ends of that passage.

15 Claims, 8 Drawing Figures

SAMPLE CHAMBER FOR GAS ANALYZER

BACKGROUND OF THE INVENTION

Duct gas analyzers which are mounted in ducts or flues typically include a source unit containing a source of suitable radiation, such as infrared, ultraviolet and visible light, mounted on one side of the duct or flue. A detector unit containing sensing devices for separating and measuring the specific wave lengths for analysis of the duct gases is mounted on the opposite side of the duct or flue. The source unit and the detector unit are typically connected by some member, such as a pipe, which serves both as an alignment fixture and as a sample cell, with apertures in the pipe allowing the duct gases to flow through the sample cell, which extends across the path of flow of the gases.

Windows of various types are typically used to isolate the source and detector units from the duct gases to protect the source, detectors and their associated electronic components. Additionally, fresh air is normally brought into the sample chamber and passed over the window faces to provide some cleansing action and to maintain a clean air region between the duct gases and the window. While this fresh air helps to keep the windows clean, over an extended time period deposits from the duct gases, particularly when these gases are gases of combustion from a furnace, build up on the window and cause errors in the qualitative and quantitative determination of the duct gas constituents. One method of correcting for this problem, caused by the deposit build-up is to block the apertures through which the duct gases enter and leave the sample cell to allow the fresh air introduced from outside to clean or purge the cell of the duct gases. During this purging the signal from the detectors may be measured to provide an indication of the error signal being caused by the deposit coating on the windows.

In one type of prior art apparatus the sample cell is in the form of a pipe having apertures aligned with the gas flow and having a pair of doors hingedly mounted to the sample cell to close off those apertures when swung to their closed position against the cell and to open those apertures when swung back away from the cell. This prior art apparatus, while providing advantages over those sample cells having no means for closing the apertures, possesses a number of disadvantages itself. For example, the doors require a relatively tight seal to achieve effective purging, a seal which is difficult to achieve and maintain over time, particularly when exposed to high temperature combustion gases. Additionally, in applications where there are large quantities of particulate matter in the duct gases, a build-up of the deposits around the door openings can prevent the doors from closing to exclude the duct gases from the chamber for purging. Such an apparatus also requires, in large scale applications, high powered fans to provide sufficient fresh air to clear the chambers. Additionally, where such sample chambers are mounted through an aperture in the duct wall, which aperture is only slightly larger than the cross-section of the closed sample chamber, a malfunction of the door closing apparatus may create sufficient mechanical interference to preclude removal of the sample chamber for service without shutting down the furnace, boiler, or other apparatus connected with the duct.

In fluid mechanics there are well known techniques for determining the pressure distribution of a flowing stream of gases at various points over a body immersed in that stream. However, none of the prior art known to the applicant has taken advantage of the kinetic energy in such a stream to assist in the operation, and particularly the purging, of a gas analyzer sample chamber.

OBJECTS OF THE INVENTION

In view of the disadvantages of the prior art sample chamber apparatus, it is an object of this invention to provide an improved sample chamber for a duct gas analyzer which will provide for compensation of deposit build-ups within the sample chamber. It is a further object of this invention to provide such apparatus which can be inserted into or removed from a duct through a relatively small aperture in the duct, regardless of whether the chamber is in an open or closed condition.

It is yet another object of this invention to provide such a sample chamber in which tight seals are not required to achieve effective purging but which utilizes the kinetic energy of the duct gases to assist in such purging.

It is still another object of this invention to provide such apparatus which is economical to manufacture and is sturdy in construction.

Briefly, this invention relates to a sample chamber for a gas analyzer for use in a duct containing the gases to be analyzed, this sample chamber including a flow directing structure and an outer housing which at least partially surrounds the flow directing structure. The flow directing structure includes a pair of spaced members opposing one another on opposite sides of the longitudinal axis of the flow directing apparatus to define a passage between the members, with the surfaces of each such member facing generally toward the other such member being convex, so that the passage between the two members is in the form of a converging-diverging throat. The outer housing also has a longitudinal axis generally parallel to the flow directing apparatus axis, and the outer housing includes at least a pair of apertures therethrough on opposite sides of a plane which includes the outer housing axis. This outer housing axis is movable, by suitable apparatus provided, between one position in which the apertures are positioned across the ends of the flow directing apparatus passage and another position in which the apertures are spaced from that passage with non-apertured portions of the outer housing positioned across the ends of the passage. In the one position the flow directing passage is open for passage of gases therethrough, and in the other outer housing position the outer housing serves to block free flow of duct gases through the flow directing passage.

BRIEF DESCRIPTION OF THE DRAWINGS

A particularly preferred embodiment of the apparatus of this invention will be described in detail below, in which.

DESCRIPTION OF A PREFERRED EMBODIMENT

Figure 1:
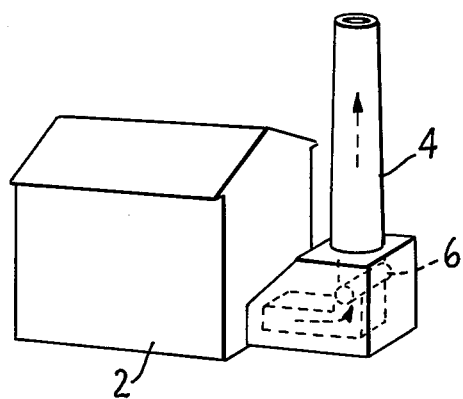
FIG. 1 is a schematic view, in perspective, of a typical application of the gas sample chamber of this invention.

In FIG. 1 a typical application of the gas sample chamber of this invention is illustrated schematically. While such a sample chamber may suitably be used in any duct for analyzing the gases flowing through that duct, it is illustrated here for use in conjunction with apparatus such as a furnace, which is not shown but is enclosed within building 2 and from which emanate combustion gases for discharge through the flue or smokestack 4. The sample chamber 6 is shown in phantom, grossly exaggerated in size for purposes of clarity of illustration, located in the flue 4. Thus it may be readily seen that the gases of combustion from the furnace flowing through the duct or flue 4 will also pass over the sample chamber 6, and a portion of these gases may be directed through the sample chamber for analysis when desired. The flow of the combustion gases over the sample chamber, which projects across the duct or flue, follows the principles of fluid mechanics.

Figure 6:
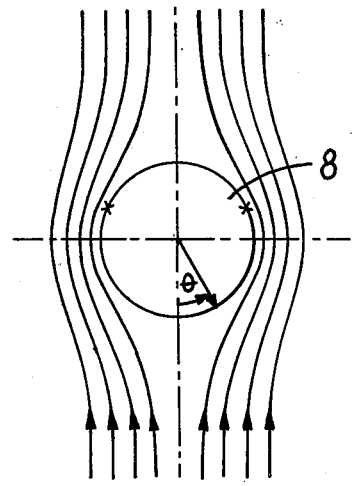
FIG. 6 is a schematic representation of a frictionless flow of fluid about a circular cylinder extending normal to that flow.
Figure 7:
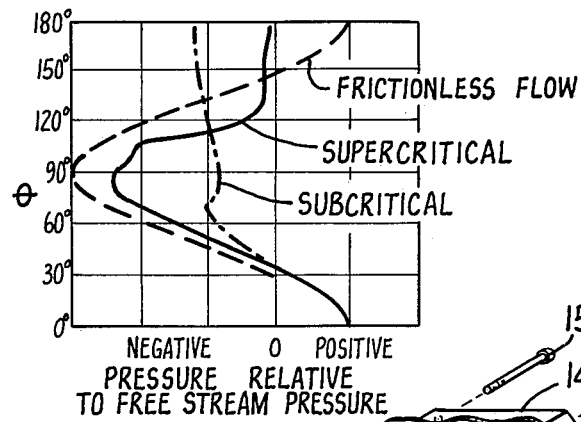
FIG. 7 is a graphical representation of pressure distributions relative to free stream pressure around the circular cylinder of FIG. 6.
Figure 8:
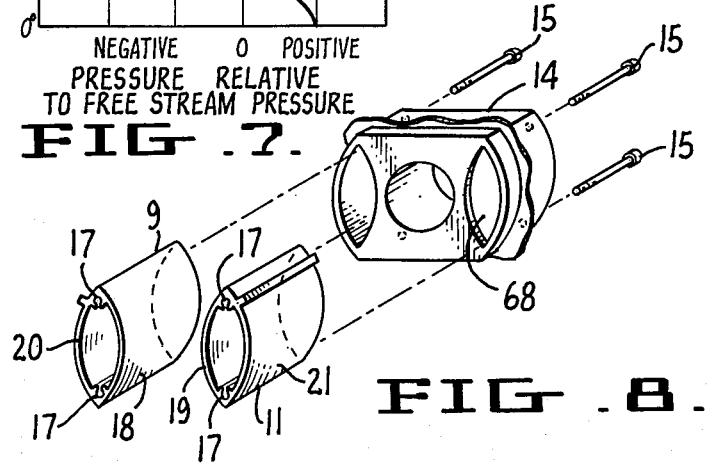
FIG. 8 is a fragmentary, exploded view of one end of the apparatus of FIG. 2, illustrating the manner of attachment of the flow directing members to the end plate.

As is well known in fluid mechanics, the effects of a fluid flow, such as a gas or liquid flow, on different bodies immersed in a moving fluid stream may be predicted through the use of a dimensionless coefficient known as the Reynolds number. The Reynolds number incorporates the fluid's velocity, density, viscosity, and a characteristic diameter of the body immersed in the fluid stream under study. It is also well known that at low fluid velocities the pressure-velocity relationship for a cylinder immersed in a moving fluid flow follows Bernoulli's equation for total energy in the stream. However, at higher Reynolds numbers, the pressure relationship becomes more complex because of friction effects. This relationship is shown in FIG. 7, which graphically illustrates the pressure distribution around half of the cylinder 8 shown in section in FIG. 6 immersed in a fluid flow. As shown in the plot of FIG. 7 of pressure relative to free stream pressure at various angles $\theta$ about the axis of cylinder 8, the pressure is positive for angles less than about 30° and greater than about 150°. These relationships apply equally to the mirror image other half of the cylinder for angles taken from the upstream stagnation point of the cylinder around to the downstream side. These relationships and plots can be found in more detail in texts such as Flachsbart, *Reports of the Aerodynamic Versuchanstalt*, Goettingen, 4th Series, p. 134 (1932).

As the velocity and Reynolds number increase, the retarding effect of fluid near the surface prevents the flow from following smoothly all the way around the body. As a result, separation of the flow from the surface occurs before the rear stagnation point (the downstream center of the cylinder in FIG. 6) is reached. The wake thus formed dissipates the kinetic energy of the fluid leaving the surface. This causes the drag coefficient to remain relatively constant over a wide range of Reynolds numbers until a critical point is reached, at which a sudden decrease occurs. At this point the greater kinetic energy of the fluid flowing around the sides of the cylinder causes the separation point to move rearward, increasing the pressures on the rear half. See Geidt, *Principles of Engineering Heat Transfer*, Van Nostrund, 1957. Thus, the pressure distribution of sub-critical and super-critical Reynolds number flows have distinct differences, as shown in FIG. 7. The preferred embodiment of the sample chamber of this invention takes advantage of these flow characteristics as described below.

Figure 2:
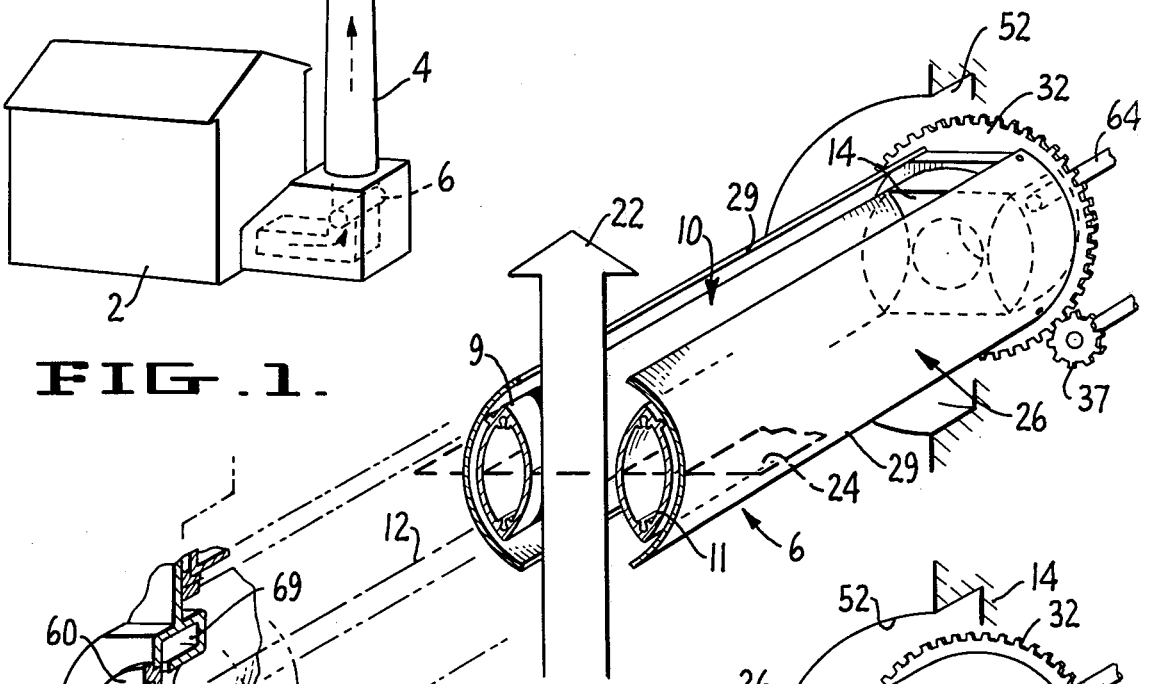
FIG. 2 is a fragmentary perspective view of a preferred embodiment of the sample chamber of this invention in an open configuration such that duct gases may freely flow through the chamber.
Figure 3:
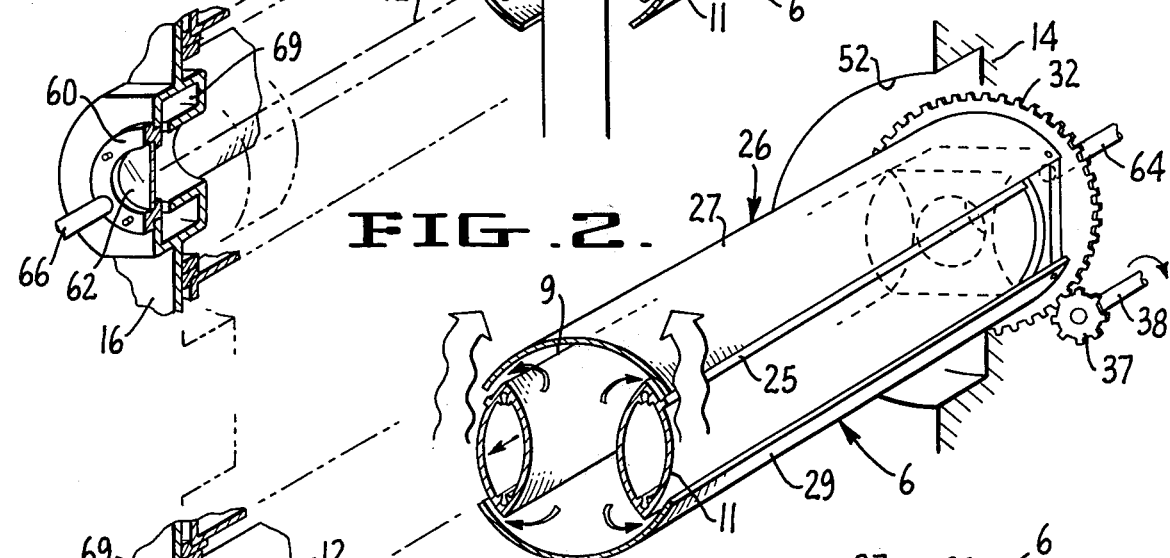
FIG. 3 is a perspective view of the apparatus of FIG. 2 in its closed configuration for purging.
Figure 4:
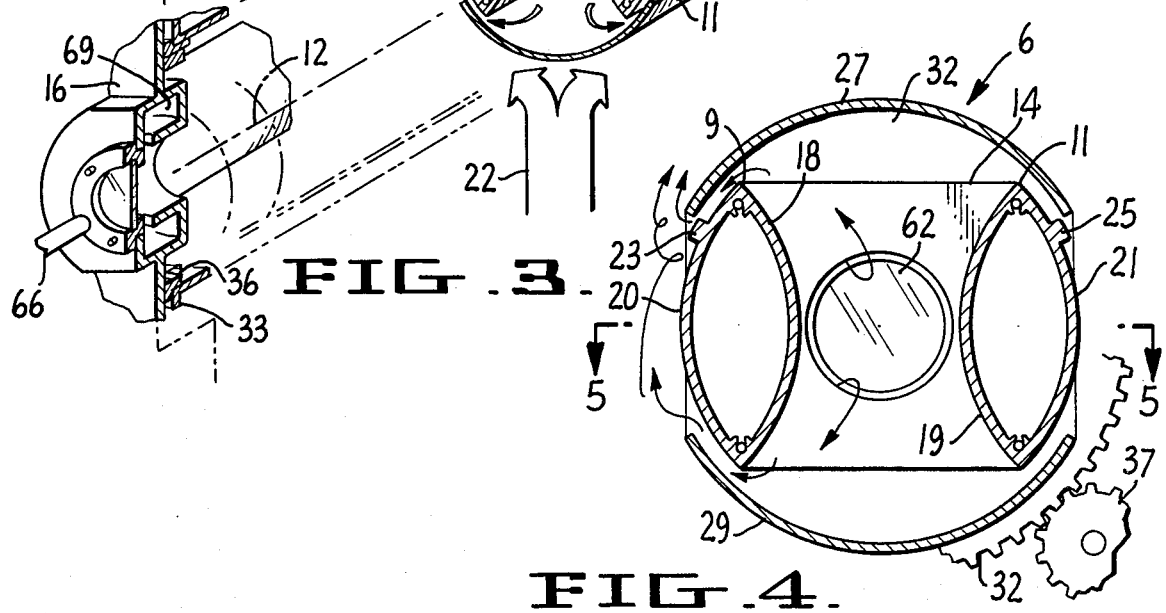
FIG. 4 is a sectional view of the apparatus of FIG. 3 looking toward the right hand end thereof.

As shown in FIG. 2, the sample chamber 6 of this preferred embodiment includes a flow directing structure 10, which suitably may be fabricated from a pair of members, such as the illustrated oval-shaped aluminum extrusions 9 and 11 shown in FIGS. 2, 3 and 4. These extrusions, spaced apart and opposing one another on opposite sides of the longitudinal axis 12 of the flow directing apparatus, are affixed at their axially outermost ends to end plates 14 and 16 in the manner indicated in FIG. 8 for end plate 14. Suitably, fastening means such as threaded fasteners extend through end plate 14 and are threaded into the relieved areas 17 on the interior of the extrusion 9 and 11. By their oval configuration and this mounting, the surfaces 18 and 19 facing generally toward one another are convex. Similarly, the surfaces 20 and 21 of the members 9 and 11, respectively, facing away from one another are also convex and, desirably may have a predetermined and substantially constant radius of curvature about the axis 12, such that these surfaces 20 and 21 form sectors of a cylinder having that predetermined radius. As shown in FIGS. 2, 3, 4 and 8, each of the members 9 and 11 also has on its radially outer surfaces 20 and 21 an extended tab or rib 23 and 25 respectively. These tabs or ribs 23 and 25 may desirably extend along the entire length of the members 9 and 11. As seen in FIG. 2, these tabs 23 and 25 are both positioned on their respective members 9 and 11 at points spaced from and on the same side of an imaginary plane 24 which extends through the sample chamber and includes the longitudinal axis 12. The purpose of these tabs 23 and 25 will be explained in detail below.

The convex configuration of the surfaces 18 and 19, which are the radially inner surfaces of the members 9 and 11 with respect to the longitudinal axis 12, form a passage between the two members in the form of a converging-diverging throat generally aligned with the direction of flow of the duct gases, indicated by the large arrow 22 in FIG. 2. This passage between the two members 9 and 11 thus permits the flow of duct gases, represented by the arrow 22, to pass through the sample chamber when it is in the configuration of FIG. 2.

Generally concentric with and at least partially surrounding the flow directing apparatus 10 is an outer housing 26. This outer housing 26 may be of numerous suitable configurations, such as apertured tubing or appropriately configured sheet material, but in this embodiment it is desirably formed of two arcuate plate members 27 and 29. These members 27 and 29, which may be formed of steel, aluminum or other suitable material, are affixed at one end (the right hand end in FIGS. 2 and 3), to a ring gear 32, which is supported by a low friction bushing 34 of nylon or other low friction material, which in turn is supported by the end plate 14. At the opposite axial ends these members 27 and 29 are affixed to a suitable ring 33 which is supported by a low friction bushing 36 similar to bushing 34, and which in turn is supported by the adjacent end plate 16. By means of these bushings 34 and 36, the outer housing 26 is thus supported for rotational movement about its longitudinal axis, which suitably may also be axis 12. Obviously, other outer housing configurations having longitudinal axes only parallel to axis 12 are equally suitable.

By this configuration of the outer housing 26, the spaces between the members 27 and 29 define a pair of apertures through this outer housing 26, with those apertures being on opposite sides of the imaginary plane 24, which includes the outer housing axis 12.

Figure 5:
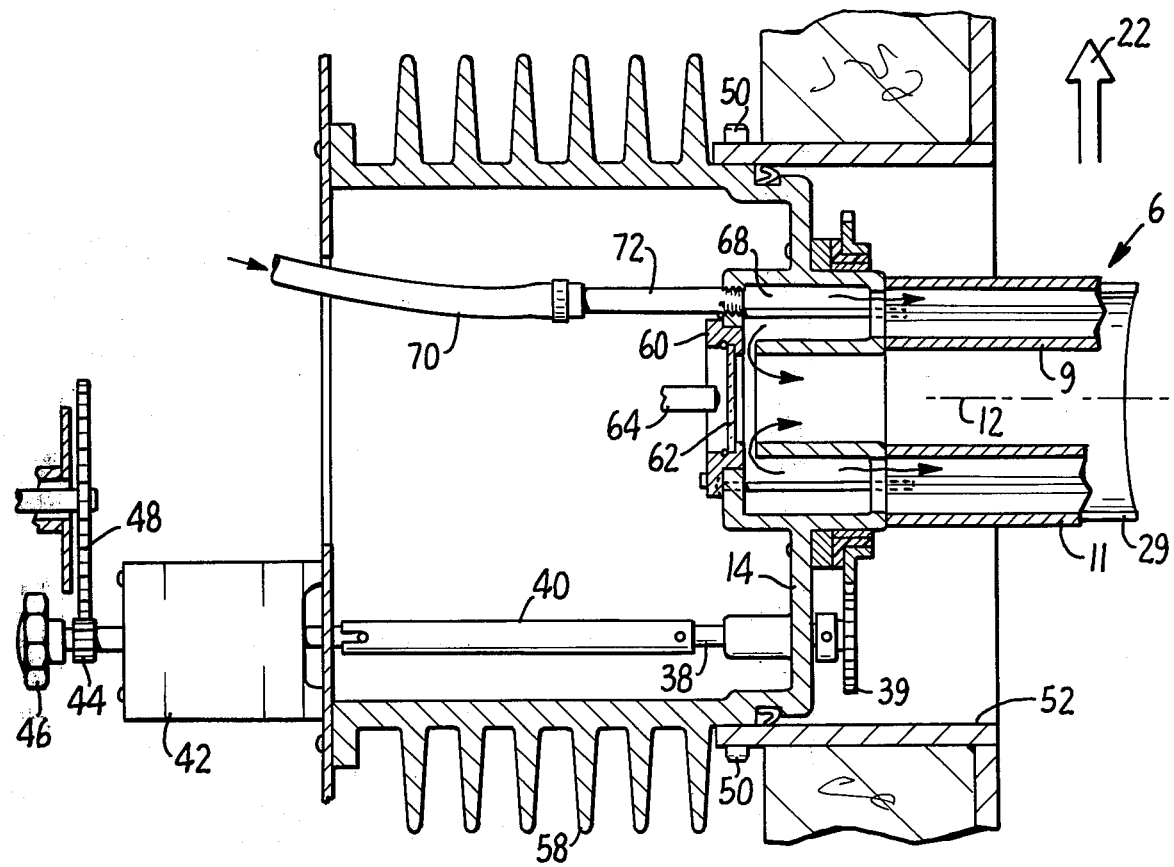
FIG. 5 is a plan view in section, with the direction of view reversed and taken through the center of the right hand end of the apparatus of FIG. 3.

Projecting through and journalled in end plate 14 is a shaft 38 to which is mounted a pinion 37 engaging gear 32, such that rotational movement of the pinion 37 will serve to drive the gear 32 and thus outer housing 26 for rotational movement about the longitudinal axis 12. As shown in FIG. 5, this shaft 38 is in turn connected to extension shaft 40. This extension shaft 40 is connected, through a suitable separable joint, to an electric drive motor 42, which provides rotational force to the shafts and the pinion 47 when suitable power and control signals are applied to that motor. At the end of motor 42 opposite the shaft connecting with extension shaft 40 may be provided another extension of the motor shaft having both a pinion 44 and a knob 46 affixed to it. The knob 46 provides for manual rotation of the pinion 37 when desired. The pinion 44 drives gear 48 which may be connected to a conventional shaft position indicator to show the rotational position of the outer housing 26.

As best shown in FIG. 5, which is a sectional plan view of the end of the chamber having the drive motor and ring gear arrangement, with the viewing direction reversed from that of FIGS. 2 and 3, the end plate 14 to which the various components are mounted may be in the form of a somewhat complex cup-like structure which may be cast of a suitable material such as mechanite. This end plate structure 14 is mounted by suitable means, such as cap screws 50, to an inset ring 52 or other suitable structure forming part of the duct or flue carrying the gases to be analyzed. At the opposite end of the sample chamber 6 the end plate 16 may be substantially similar to the portion of end plate 14 inward of a point immediately inward of the cooling fins 58, thus providing a sufficiently small diameter that it may be passed through a similar inset ring 52. Thus, the sample chamber 6 of this preferred embodiment extends inwardly of the flue from one side thereof and desirably extends all the way across to the other side and through that other side, although other embodiments could extend from only one side of the duct.

At the radial center of each of the end plate structures 14 and 16 is provided a removably mounted window including a bezel 60 and a window 62 which is transparent to the radiation of interest. Adjacent the window 62, which suitably is normal to the axis 12 and is outside the sample chamber at one end, is provided a suitable and conventional source for the desired radiation, with a conventional detector 66 for that type of radiation being correspondingly positioned outside the window 62 at the opposite end of the chamber. Alternatively, both the radiation source 64 and the detector 66 could be positioned side-by-side at one end of the chamber with the window 62 at the opposite end of the chamber being replaced with a reflective element, such as a mirror, so that the radiation from the source traverses the longitudinal extent of the chamber twice, from the source to the reflective element and from the reflective element back to the detector.

Adjacent the window structure mounted to end plate 14 is provided an air plenum 68, with a corresponding air plenum 69 being provided adjacent the opposite window structure. Both of these plenums 68 and 69 are generally concentric with the windows 62 and may suitably form an integral portion of the respective end plates 14 and 16. At the end of the sample chamber containing the drive motor 42 a source of pressurized air (not shown) is connected through tube 70 and pipe 72 to plenum 68. By virtue of the communication of that plenum 68 with the hollow interior of the flow directing members 9 and 11, as shown in FIG. 5, a portion of that pressurized air supplied to plenum 68 may be conducted through those members 9 and 11 to the plenum 69 associated with opposite end plate 16, which also communicates with the hollow interior of the members 9 and 11. Thus, both of these plenum chambers 68 and 69 provide the clean air which is used to purge the sample chamber, and particularly the passage between the two flow directing members 9 and 11, of unwanted gases from the duct or flue in a manner to be described below.

From the foregoing description of the apparatus of this invention, the manner of its operation may now be seen, with particular respect to FIGS. 2, 3 and 4. As shown in FIGS. 2 and 3, the outer housing 26 is supported on the bushings 34 and 36 at its opposite axial ends. By virtue of this support the outer housing 26 in this embodiment is movable, by means of rotation about axis 12, between one position in which the apertures, defined by the longitudinally extending gaps between the adjacent edges of the arcuate members 27 and 29, are positioned across the ends of the flow directing apparatus passage, and another position in which those apertures are spaced from the passage with non-apertured portions of the outer housing being positioned across the ends of the flow directing structure. In the one position, shown in FIG. 2, the flow of gases indicated by the arrow 22 may pass freely through the outer housing apertures and thus through the converging-diverging throat and passage between the two flow directing members 9 and 11. When the outer housing 26 is moved, by rotation in the preferred embodiment, to the other position illustrated in FIG. 3, with its apertures generally facing transversely of the direction of flow 22 of the gases in the flue or duct, the passage between the two flow directing members 9 and 11 is covered by the outer housing which deflects the flue gases around the sample chamber apparatus.

The sample chamber of this invention and particularly the outer housing 26 and the radially outer surfaces 20 and 21 of the flow directing member are configured and dimensioned with respect to the size of the duct and the rate of flow, density and viscosity of the gases flowing therethrough such that the Reynolds number for that flow and this apparatus remains in the sub-critical region at all times when the outer housing is in its other position, closing off the passage between the flow directing members. For example, for a gas having a density of 0.075 lb/ft$^3$, a viscosity of $0.35 \times 10^{-6}$ lb-sec/ft$^2$ and flowing at 50 ft/sec, the sample chamber diameter, particularly the outer diameter of the outer housing, might suitably be about 6.5 inches. Thus, the pressure distribution around the sample chamber with respect to the free stream pressure may be that shown in the diagrams of FIGS. 7 and 8. From FIG. 7 it may be seen that the pressure of the stream on the outer surface of the chamber remains negative for all points around the chamber behind about 35° from the stagnation point facing dead ahead into the stream of the duct gases. Thus, where the upstream edges of the apertures between the outer housing members 27 and 29 lie more than about 35° behind that stagnation point, such as about 45° or more for the preferred embodiment described above, the pressure exerted by the gas stream as it flows by those apertures is less than the free stream pressure. Consequently, the flowing gases tend not to attempt to enter the chamber through the apertures in the outer housing when they are positioned as shown in FIGS. 3 and 4, but rather tend to evacuate the interior of the sample chamber due to the pressure differential at those points with respect to the free stream pressure. Such evacuation, along with the fresh air introduced through the plenum chambers 68 and 69 serves to purge any of the duct gases from the sample chamber when the outer housing 26 is moved to the position illustrated in FIGS. 3 and 4.

Tabs 23 and 25, described above, can be seen in FIGS. 3 and 4 to be positioned on the flow directing members 9 and 11 such that, when outer housing 26 is in its purging position (FIGS. 3 and 4) these tabs 23 and 25 are just upstream from the downstream edge of the apertures in the outer housing. Thus, these tabs serve to create additional turbulence in the portion of the gas stream flowing over the sample chamber, which flow may bear against the portion of the outer surface of the inner chamber which is exposed to the outer housing apertures. Thus, any such duct gases are deflected away from the downstream edge of the outer housing apertures and create an additional low pressure area there to effect additional purging of the gases from the interior of the chamber and to block any migrant flow of duct gases into the sample chamber, as indicated by the various arrows in FIGS. 3 and 4. By virtue of these pressure differentials, it may be seen that the spacing of the radially outer surfaces 20 and 21 from the radially inner surfaces of the outer housing members 27 and 29 facilitates the purging of the interior of the sample chamber through the flow directing passage and thence out the outer housing apertures. This arrangement eliminates the need for any tight seals which might degrade or be otherwise comprised by particulate matter in the stream of duct gases. Thus, any build-ups of deposits of such particulate matter will not prevent this sample chamber from functioning in the desired manner. Additionally, the cylindrical configuration of the outer housing eliminates the problems of mechanical interference when inserting or removing the chamber through the side of the duct. The provision in the sample chamber of this apparatus for the use of the kinetic energy of the flue gases to assist in the purging has the additional benefit of avoiding the need for powerful blowers supplying high pressure air to the plenum chambers 68 and 69.

The foregoing detailed description relates to a particularly preferred embodiment of the apparatus of this invention and thus is intended only to illustrate the principles of the invention, which may apply equally well to numerous other variations and modifications which will readily occur to those skilled in the art. Such variations and modifications might include, for example, the use of structures other than aluminum extrusion for the flow directing members, and the use of members having various other configurations which are within the scope of the invention. Similarly, other structures might be used for the outer housing, such as a casting or a section of pipe or tubing having the desired apertures cut through the walls. These and all other variations and modifications encompassed within the scope of the claims appended hereto are considered equally to be a part of this invention. Accordingly, the scope of this invention is to be determined solely by the claims appended hereto.

What is claimed is:

1. A sample chamber for a gas analyzer for use in a duct containing the gases to be analyzed, comprising
   flow directing means having a longitudinal axis extending generally centrally thereof, said flow directing means including a pair of spaced members opposing one another on opposite sides of said axis to define a passage between said members, with the surfaces each said member facing generally toward the other said member being convex, such that the passage between the two members is in the form of a converging-diverging throat;
   outer housing means at least partially surrounding said flow directing means and having a longitudinal axis generally parallel to said flow directing means axis, said outer housing means having at least a pair of apertures therethrough on opposite sides of a plane which includes said outer housing axis, and said outer housing means being movable between one position in which said apertures are positioned across the ends of flow directing means passage and another position in which said apertures are spaced from said passage with non-apertured portions of said outer housing positioned across the ends of said flow directing means passage whereby, when the outer housing means is in the one position its apertures provide for free flow of gases through flow directing means passage and, when in the other position, the outer housing means serves to block free flow of duct gases through the passage; and
   means for moving said outer housing means between said one position and said other position.

2. The sample chamber of claim 1 wherein the surfaces of each said flow directing means member facing away from the other said member is also convex.

3. The sample chamber of claim 2 wherein said surfaces of said flow directing means members facing away from one another have a predetermined and substantially constant radius of curvature about said flow directing axis and define the radially outer surfaces of said flow directing means, whereby the radially outer surfaces of the flow directing means form sectors of a cylinder having that predetermined radius.

4. The sample chamber of claim 3 wherein said outer housing means comprises a pair of arcuate members extending parallel to said outer housing axis and supported adjacent their axially outermost ends, whereby the outer housing means is in the form of an apertured, hollow cylindrical structure having radially outer and radially inner surfaces.

5. The sample chamber of claim 4 wherein the movement of said outer housing means between said one position and said other position comprises rotation about said outer housing means axis.

6. The sample chamber of claim 4 wherein the radially outer surfaces of said flow directing means are spaced radially from said radially inner surfaces of said outer housing means.

7. The sample chamber of claim 6 further comprising tab means extending longitudinally along said flow directing means radially outer surfaces and projecting radially toward said outer housing means radially inner surface, said tab means being positioned on each said member spaced from and on the same side of a plane which includes said flow directing means axis and is transverse to said flow directing means passage.

8. The sample chamber of claim 1 wherein at least one said flow directing means member includes a passage extending internally of said member from one end of said member longitudinally to the opposite end of said member.

9. The sample chamber of claim 1 further comprising window means at each of the opposed axial ends of said flow directing means, with each said window means facing the other along said flow directing means passage.

10. In a duct having a gas of predetermined density and viscosity flowing therethrough at a predetermined velocity, a sample chamber for a gas analyzer extending into said duct from one side thereof for analyzing the gases in such duct, comprising flow directing means having a longitudinal axis extending generally centrally thereof and transversely to the flow of gases in the duct, said flow directing means including a pair of spaced members opposing one another on opposite sides of said axis to define a passage between said members generally aligned with the flow of gases in the duct, with the surfaces each said member facing generally toward the other said member being convex, such that the passage between the two members is in the form of a converging-diverging throat;

outer housing means at least partially surrounding said flow directing means and having a longitudinal axis generally parallel to said flow directing means axis, said outer housing means having at least a pair of apertures therethrough on opposite sides of a plane which includes said outer housing axis, and said outer housing means being movable between one position in which said apertures are positioned across the ends of flow directing means passage and another position in which said apertures face generally transverse to the flow of gases in the duct and are spaced from said passage with non-apertured portions of said outer housing positioned across the ends of said flow directing means passage whereby, when the outer housing means is in the one position its apertures provide for free flow of the duct gases through flow directing means passage and, when in the other position, the outer housing means serves to block free flow of the gases through the passage; and means for moving said outer housing means between said one position and said other position.

11. The sample chamber of claim 10 wherein said outer housing means and said flow directing means are configured and dimensioned such that the Reynolds number for said flow of duct gases over said outer housing means and said inner chamber means when said outer housing means is in said other position is sub-critical.

12. The sample chamber of claim 11 wherein said outer housing means comprises a hollow, apertured generally right circular cylindrical structure having radially outer surfaces and radially inner surfaces and wherein the surfaces of said flow directing means facing outwardly from its said longitudinal axis comprise portions of a generally right circular cylinder, with said flow directing means outwardly facing surfaces being spaced from the radially inner surfaces of said outer housing means.

13. The sample chamber of claim 12 further comprising tab means projecting radially outwardly from said outward facing surfaces of said flow directing means, said tab means being positioned such that, when said outer housing means is in said other position with said outer housing apertures facing generally transverse to the flow of gases through the duct, said tab means are upstream from the downstream edge of each of said outer housing apertures with respect to said flow of gases, whereby the tab means may serve to create turbulence in the gases flowing over the outward facing surface of the flow directing means which is exposed through the outer housing apertures.

14. The sample chamber of claim 13 wherein said tab means extend longitudinally on said flow directing means for substantially the entire longitudinal extent of said outer housing means apertures.

15. The sample chamber of claim 10 wherein each said flow directing means member comprises a length of an aluminum extrusion.

* * * * *